United States Patent [19]

Warriner

[11] Patent Number: Plant 6,446

[45] Date of Patent: Dec. 6, 1988

[54] ROSE PLANT JACPLUM

[75] Inventor: William A. Warriner, Tustin, Calif.

[73] Assignee: Jackson & Perkins Co., Medford, Oreg.

[21] Appl. No.: 945,251

[22] Filed: Dec. 22, 1986

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Majestic, Gallagher, Parsons & Siebert

[57] ABSTRACT

A hybrid tea rose variety having photosensitivity, an unusual blend of dark and medium lavender colors, pleasant fragrance, vigor and profuse display of flowers, and upright habit of growth.

1 Drawing Sheet

This present invention relates to a new and distinct variety of rose plant of the hybrid tea class which was originated by crossing the variety Heirloom, U.S. Plant Pat. No. 3,234, with the variety Color Magic, U.S. Plant Pat. No. 3,998.

The primary objective of this breeding was to produce a new rose variety combining the lavender coloration of Heirloom with the blending of colors and photosensitivity found in the variety Color Magic. This objective was substantially achieved along with other desirable improvements as evidenced by the following unique combination of characteristics which are outstanding in the new variety and which distinguish it from its parents as well as from all other varieties of which I am aware:

1. Unique, dark lavender, high-centered flower;
2. Pleasant fragrance;
3. Photosensitivity (darkens in full sun);
4. Profuse flowering; and
5. Vigorous, upright growth.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Heirloom, U.S. Plant Pat. No. 3,234.

*Pollen parent.*—Color Magic, U.S. Plant Pat. No. 3,998.

Classification:

*Botanical.*—Rosa hybrid.

*Commercial.*—Hybrid tea.

FLOWER

Observations made from specimens grown in a greenhouse at Irvine, Calif. in September and October, 1986.

Blooming habit: Continuous.

Bud:

*Size.*—1½" when petals start to unfurl.

*Form.*—Long, pointed ovoid.

*Color.*—When sepals first divide, Red Group 53B to C on the petal edges with a much paler color on the rest of the petal ranging from 54B to 54C at the petal base; when half blown, upper side of petals ranging from Red 53B on the petal margins, becoming paler toward the petal base (Red 53C to Red 53D); lower side of petals Red 54B to Red 54C.

*Sepals.*—Color: Green Group 138B overlaid with a purple cast. Three appendaged sepals normally to heavily appendaged. Two unappendaged sepals hairy edge.

*Receptacle.*—Color: Green Group 138A with some purple splashes. Shape: Funnel. Size: Medium. Surface: Hairy.

*Peduncle.*—Length: Medium. Surface: Glandular. Color: Medium green and bronzy. Strength: Stiff, erect.

Open bloom:

*Size.*—Large. Average open size 5".

*Borne.*—Singly.

*Stems.*—Long, strong.

*Form.*—When first open, high center. Permanence: Retains its form to the end; outer petal edges slightly curled and quilled.

*Petalage.*—Number of petals under normal conditions: 45–50.

*Color.*—Center of flower: Upper side of petals, ranges from Red Group 53B on the petal margins to 53C near the petal base; reverse side of petals, Red Group 54B to 54C. Base of petals, small yellow half moon, Yellow Group 2B. Major color: Red Group 53B.

*Variegations.*—None.

*Discoloration.*—General tonality at end of first day: None. Third day: A general darkening of color.

*Fragrance.*—Moderate.

Petals:

*Texture.*—Thick.

*Shape.*—Round.

*Form.*—Tips slightly recurved, edges slightly quilled.

*Arrangement.*—Imbricated.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: Yellowish red.

*Pollen.*—Lemon yellow.

*Styles.*—Color: Reddish.

*Stigmas.*—Color: Greenish white.

PLANT

Form: Bush.

Growth: Vigorous, upright.

Foliage:

*Number of leaflets on normal mid-stem leaves.*—5 to 7.

*Size.*—Medium.

*Quantity.*—Normal.

*Color.*—New foliage: Reddish. Old foliage: Dark green.

Leaflets:

*Shape.*—Oval pointed.

*Texture.*—Glossy, smooth.

*Edge.*—Serrated.

*Serration.*—Single, medium.

*Petiole.*—Rachis: Color: Reddish. Underside: Smooth, with a few prickles.

*Stipules.*—Long, serrated.

*Disease resistance.*—Susceptible to mildew, under normal growing conditions at Irvine, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its photosensitivity, its unusual blend of dark and medium lavender colors, its pleasant fragrance, its vigor and profuse display of flowers, and its upright habit of growth.

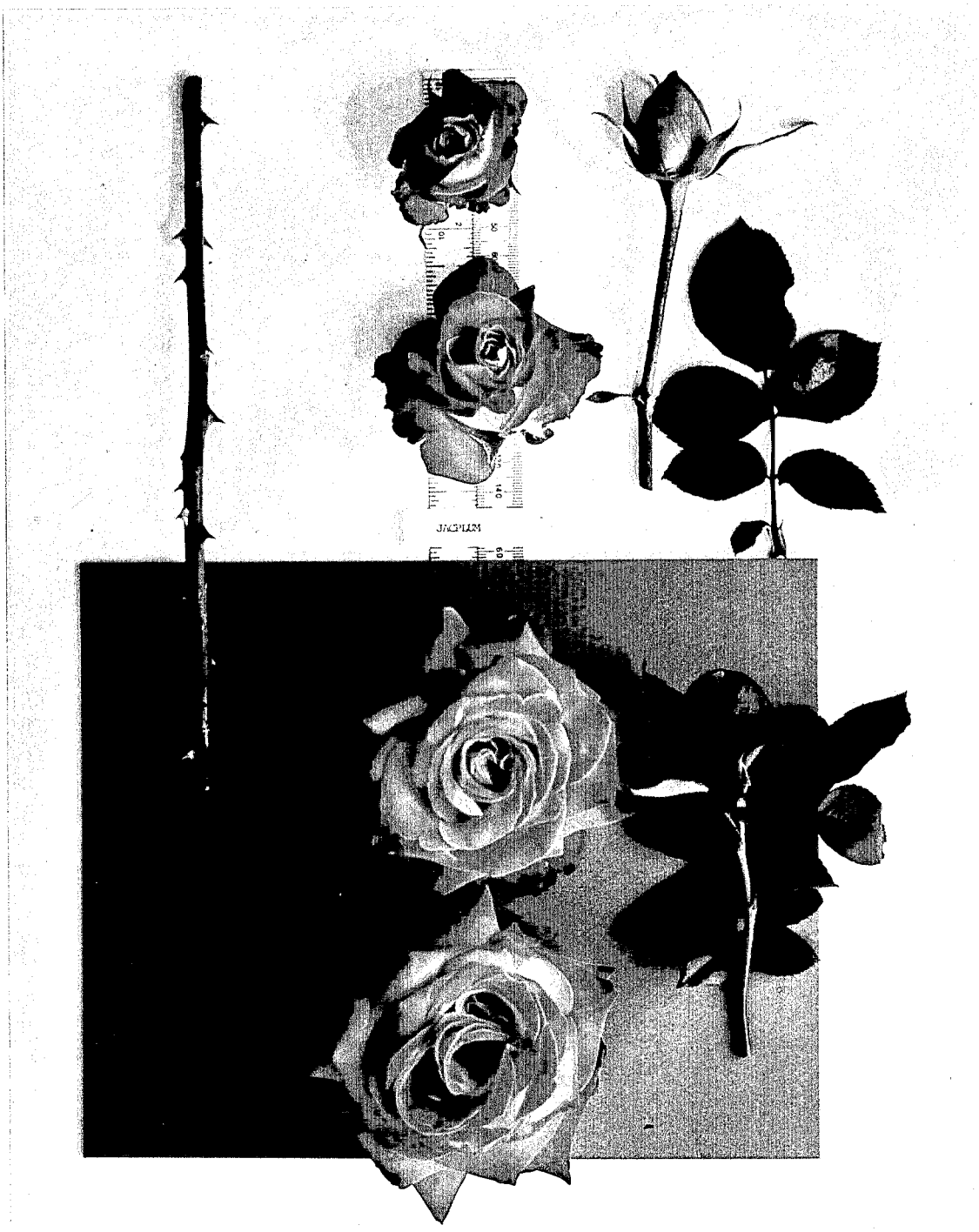

* * * * *